United States Patent [19]

Tomcufcik et al.

[11] Patent Number: 4,977,189

[45] Date of Patent: Dec. 11, 1990

[54] SUBSTITUTED GUANIDINEDICARBONYL DERIVATIVES

[75] Inventors: Andrew S. Tomcufcik, Old Tappan, N.J.; James S. Dixon, Malvern, Pa.; Joseph W. Epstein, Monroe, N.Y.; Gary H. Birnberg, Tuxedo, N.Y.; William J. Fanshawe, Pearl River, N.Y.

[73] Assignee: American Cyanamid Company, Stamford, Conn.

[21] Appl. No.: 217,518

[22] Filed: Jul. 11, 1988

Related U.S. Application Data

[63] Continuation-in-part of Ser. No. 860,406, May 7, 1986, abandoned.

[51] Int. Cl.$^5$ ............... C07C 311/47; C07C 279/22; A61K 31/18; A61K 31/165

[52] U.S. Cl. ................... 514/603; 514/616; 564/153; 564/157; 564/86; 260/404.5

[58] Field of Search ............ 564/153, 157, 86; 514/603, 616; 260/404.5 G

[56] References Cited

U.S. PATENT DOCUMENTS 3,535,256 10/1970 Siano et al. .................. 524/195
3,914,306 10/1975 Douglas et al. ............ 564/157 X R

FOREIGN PATENT DOCUMENTS 2020937 11/1971 Fed. Rep. of Germany ...... 564/157

Primary Examiner—Carolyn S. Elmore
Attorney, Agent, or Firm—Thomas S. Szatkowski

[57] ABSTRACT

This disclosure describes novel substituted guanidinedicarbonyl derivatives which possess anxiolytic activity and are also useful as agents for the treatment of cognitive and related neural behavioral problems in mammals.

17 Claims, 4 Drawing Sheets

SUBSTITUTED GUANIDINEDICARBONYL DERIVATIVES

CROSS REFERENCE TO RELATED APPLICATION

This application is a continuation-in-part of our co-pending application Ser. No. 860,406, filed May 7, 1986 now abandoned.

BRIEF SUMMARY OF THE INVENTION

The present invention relates to new organic compounds and, more particularly, is concerned with novel substituted guanidinedicarbonyl derivatives useful as anxiolytic agents and as agents for the treatment of cognitive and related neural behavioral problems in mammals, to a process for their preparation, and to pharmaceutical compositions containing them.

The substituted guanidinedicarbonyl derivatives of the present invention may be represented by the following general formula:

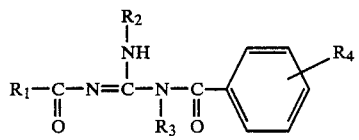

wherein $R_1$ is alkyl($C_1$–$C_{10}$), biphenyl, phenylalkyl($C_1$–$C_3$), phenoxyalkyl($C_1$–$C_3$), naphthyl, cinnamenyl, adamantyl, cycloalkenyl($C_5$–$C_7$) or a moiety of the formula:

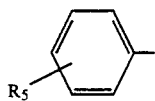

wherein $R_5$ is hydrogen, halogen, trifluoromethyl, nitro, alkyl($C_1$–$C_6$) or alkoxy($C_1$–$C_3$); $R_2$ is dialkyl($C_1$–$C_3$)aminoalkyl($C_1$–$C_3$) or moieties of the formulae:

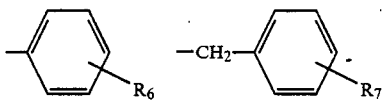

wherein $R_6$ is carbamoyl, alkyl($C_1$–$C_9$aminocarbonyl or a dialkyl($C_1$–$C_3$)aminocarbonyl and $R_7$ is carbamoyl or sulfamoyl; $R_3$ is hydrogen or alkyl($C_1$–$C_6$); and $R_4$ is hydrogen, halogen, trifluromethyl, nitro, alkyl($C_1$–$C_6$) or alkoxy($C_1$–$C_3$).

This invention also pertains to new compositions of matter containing the above-defined, novel, substituted guanidinedicarbonyl derivatives which are useful as anxiolytic agents and as agents for the treatment of cognitive and related neural behavioral problems in mammals, and the methods for treating anxiety and cognitive and related neural behavioral problems in mammals therewith and to the chemical synthesis of the novel compounds disclosed herein.

DETAILED DESCRIPTION OF THE INVENTION

The novel compounds of the present invention are, in general, obtainable as white or off-white crystalline solids having characteristic melting points and adsorption spectra.

Figure 1:
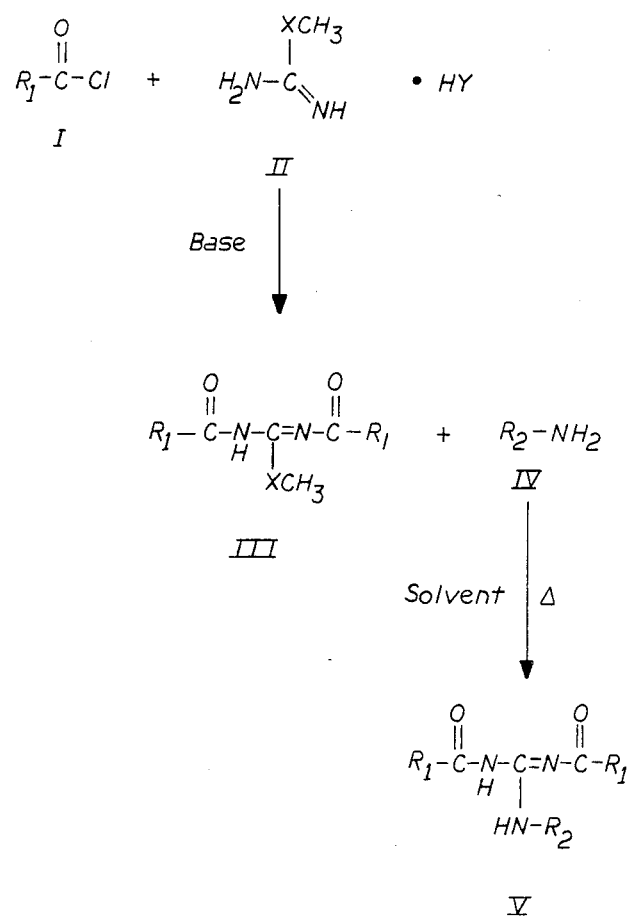
Figure 2:
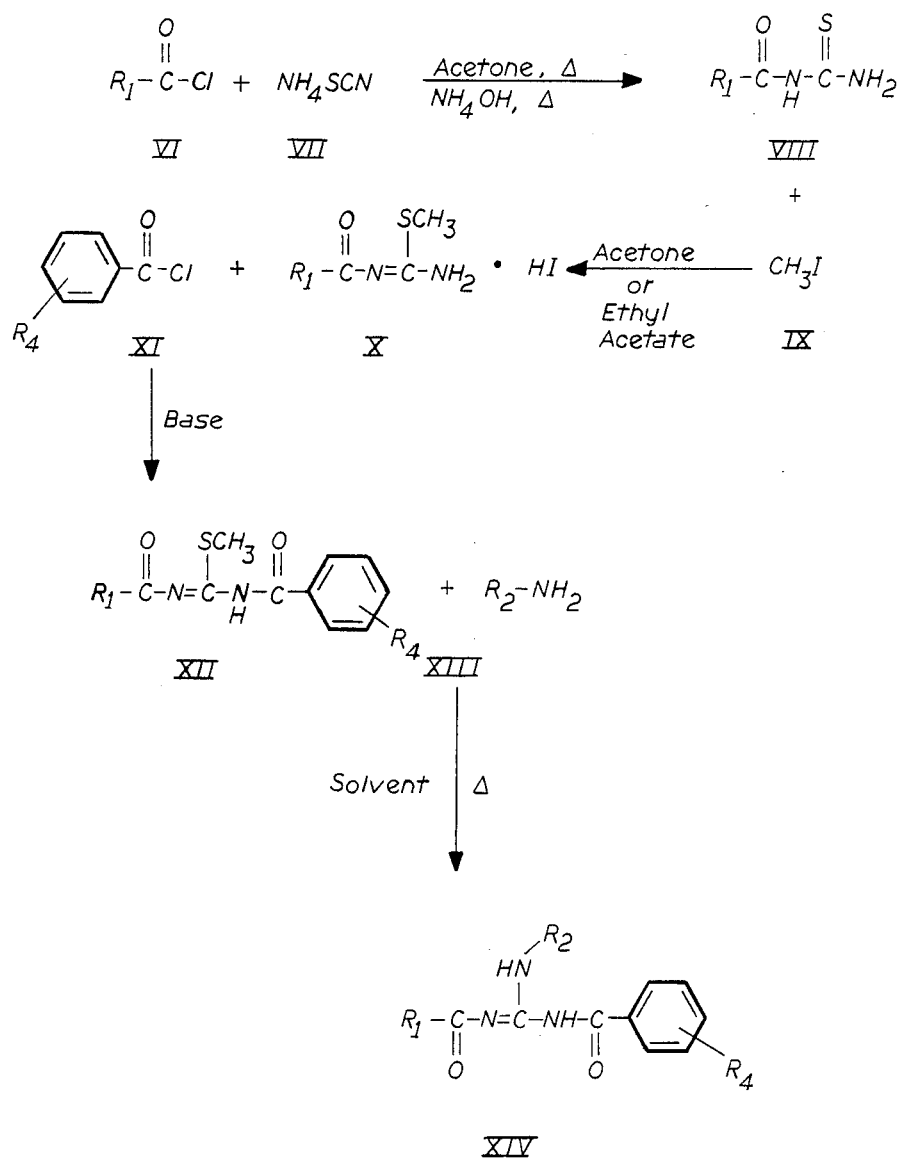
Figure 3:
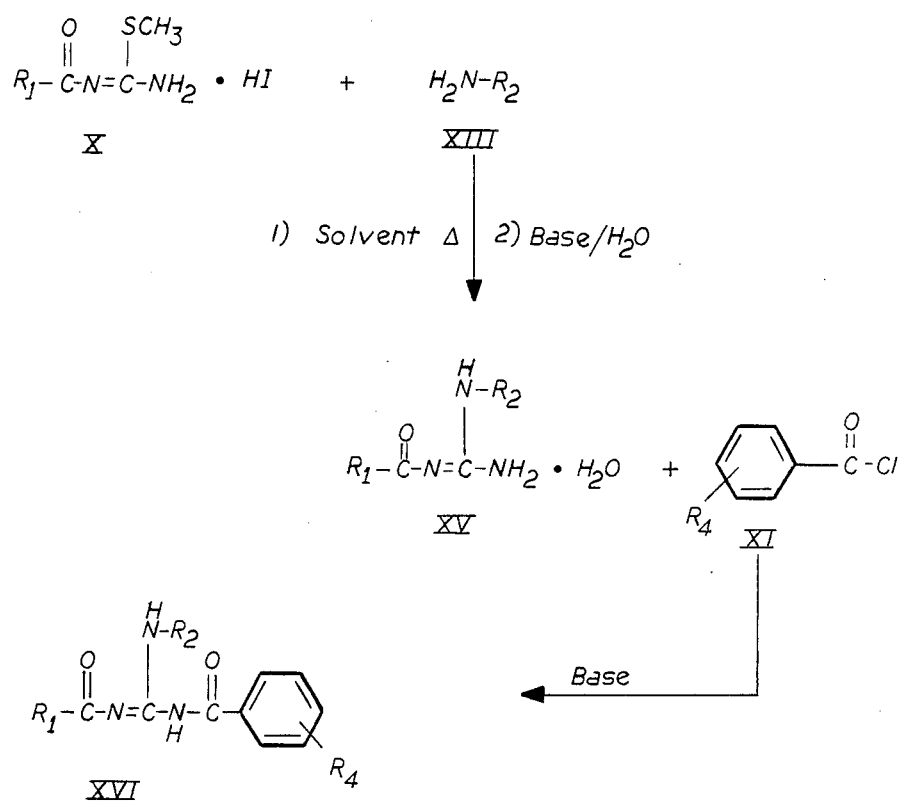
Figure 4:
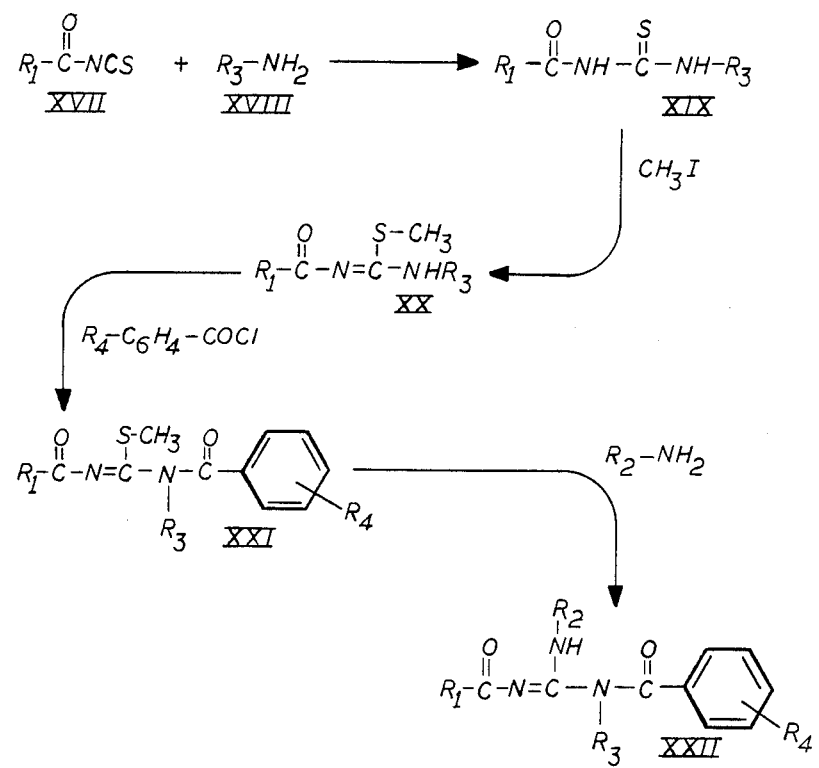

The novel 1,2-unsubstituted and substituted alkanoyl, aroyl or heteroaroyl-3-alkyl, (dialklamino)alkyl or aryl [carbamoyl, alkylaminocarbonyl or dialkylaminocarbonyl], substituted guanidine compounds of the present invention may be prepared described in the reaction schemes found in FIGS. 1 to 4.

In Scheme 1 (FIG. 1) X is O or S, and HY is an acid such as $H_2SO_4$, HI, HBr, HCl and the like and where $R_1$ is

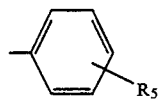

wherein $R_5$ is as hereinbefore defined; and $R_2$ is

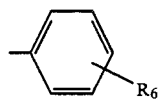

wherein $R_6$ is as hereinbefore defined.

In Scheme 1 (FIG. 1) the reaction of benzoyl chloride or a substituted benzoyl chloride I with II, a 2-alkyl-2-thiopseudourea salt, e.g. 2-methyl-2-thiopseudourea sulfate, or an O-alkylisourea salt, e.g. O-methylisourea hydrogen sulfate in a basic solvent, e.g. pyridine, gives the corresponding symmetrical 1,3-dibenzoyl-2-methylisothiourea III. When the isothiourea or isourea III is heated at reflux for 18–60 hours in a solvent such as isopropyl alcohol, pyridine, toluene, or the like with an amine IV, for example, 2-aminobenzamide, 4-aminobenzamide, 2-(methylamino)benzamide or 4-(methylamino)benzamide and the like, corresponding symmetrical 1,2-substituted or unsubstituted dibenzoyl-3-[(carbamoyl)phenyl]guanidine products V are obtained.

In Scheme 2 (FIG. 2) the reaction of an unsubstituted or substituted aroyl or heteroaroyl chloride VI with ammonium thiocyanate VII at the reflux temperature in acetone for about 15 minutes, is followed by the gradual addition of concentrated ammonium hydroxide while maintaining reflux for about 20 minutes, then with further refluxing for a total of about one hour. The cooled reaction mixture is added to water to precipitate the corresponding N-(aminothioxomethyl)benzamide VIII. The benzamide VIII in acetone is heated at reflux in the presence of methyl iodide for about 2 hours and is filtered while hot and washed with solvent to obtain the corresponding aroyl or heteroaroyl carbamimidothioic acid, methyl ester monohydriodide X. The methyl ester monohydriodide X in pyridine is then stirred with an unsubstituted or substituted aroyl chloride XI for 1–4 hours. The reaction mixture is poured into water to yield the corresponding N-aroyl or heteroaroyl-N'-[aroyl]carbamimidothioic acid, methyl ester intermediate compound XII. The methyl ester intermediate XII in a solvent such as isopropyl alcohol is refluxed for one hour to 9 days with an appropriate amine XIII such as 2-aminobenzamide, 4-aminobenzamide, 2-(methylamino)benzamide, 4-(methylamino)benzamide or a (dialkylamino)alkylamine such as N,N-diethylethylenediamine and the like to give the corresponding symmetrical or unsymmeterical guanidinedicarbonyl derivatives XIV.

In Scheme 3 (FIG. 3) the reaction of an aroyl or heteroaroyl carbamimidothioic acid, methyl ester monohydriodide X with an amine XIII such as 2-aminobenzamide or 4-aminobenzamide in a solvent such as isopropyl alcohol at the reflux temperature for 24–60 hours gives the corresponding N-[[[(aminocarbonyl)-phenyl] amino]iminomethyl]benzamide XV. The compound XV in a solvent such as pyridine is reacted with an aroyl or heteroaroyl chloride by stirring at room temperature for 2–8 hours. The reaction is quenched in water and the symmetrical or unsymmetrical guanidinedicarbonyl product XVI is obtained. The reaction conditions for the sequence of steps outlined in reaction scheme 4 (FIG. 4) are essentially the same as for the corresponding steps in SCHEME 2 except that $R_3$—$NH_2$ is substituted for the $NH_4OH$ employed in SCHEME 2.

Certain of the novel compounds of the present invention possess central-nervous-system activity at nontoxic doses and as such may be useful as anxiolytic agents in that they produce certain responses in standard tests with laboratory animals which are known to correlate well with relief of anxiety in man. The compounds have been tested pharmacologically and have been found to have such properties with a desireable wide spread between doses producing anxiolytic activity and toxic symptoms.

A test utilized for the determination of anxiolytic activity is the measurement of the ability of test compounds to inhibit the binding of tritiated benzodiazepines to brain-specific recptors of warm-blooded animals. A modification of the method described by R. F. Squires, et al., Nature, 266, No. 21, pg 732 (April, 1977) and H. Mohler, et al., Science, 198, pg 849 (1977) was employed.

Male albino rats (Wistar strain, weighing 150–200 g each) were used. The test compounds were solubilized in either dimethylformamide, acetic acid, ethanol or hydrochloric acid.

Whole cortex of rats was homogenized gently in 20 volumes of ice-cold 0.32M sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume in hypotonic 50 mM Tris.HCl (pH 7.4), or (2) resuspended in one-half the original volume in hypotonic 10 mM Tris.HCl (pH 7.4) and frozen ($-20°$ C.) until time of use. Frozen $P_2$ preparations were thawed and resuspended in four times the original homogenizing volume at time of assay.

The binding assay consisted of 300 $\mu$l of the $P_2$-fraction suspension (0.2–0.4 mg protein), 100 $\mu$l of test drug and 100 $\mu$l of $^3$H-diazepam (1.5 nM, final concentration) or $^3$H-flunitrazepam (1.0 nM, final concentration) which was added to 1.5 ml of 50 mM Tris.HCl (pH 7.4). Non-specific binding controls and total binding controls d 100 $\mu$l of diazepam (3 $\mu$M final concentration) and 100 $\mu$l of deionized water, respectively, in place of the test compound. Incubation for 30 minutes proceeded in ice and was terminated by filtration, under vacuum, through glass fiber filters. The filters were washed twice with 5 ml of ice-cold 50 mM Tris.HCl (pH 7.4) and placed in scintillation vials. After drying at 50°–60° C. for 30 minutes, 10 ml of diluent was added and the radioactivity determined in a scintillation counter.

Inhibition of binding was calculated by the difference between total binding and binding in the presence of test compound, divided by the total binding, X 100.

The results of this test on representative compounds of this invention appear in Table I.

TABLE I

| Inhibition of the Binding of $^3$H-Benzodiazepine to Brain-Specific Receptors of Rats | |
|---|---|
| Compound | % Inhibition |
| N,N'-[[4- 9Aminocarbonyl)phenyl]carbonimidoyl]bis[3-methylbenzamide] | 25 |
| N,N'-[[4-(Aminocarbonyl)phenyl]carbonimidoyl]bis[4-methoxybenzamide] | 17 |
| N,N'[[3-(Aminocarbonyl)phenyl]carbonimidoyl]bis[3-methylbenzamide] | 17 |
| N,N'-[[4-(Octylamino)carbonyl]phenyl]carbonimidoyl]bis[3-methylbenzamide] | 16 |
| N,N'[[4-[(Methylamino)carbonyl]phenyl]carbonimidoyl]bis[3-methylbenzamide] | 17 |
| 4-[[Bis[(3-methylbenzoyl)amino]methylene]-amino]-N,N-dimethylbenzamide | 29 |
| 4-[[(Benzoylamino)(benzoylimino)methyl]-amino]-N,N-dimethylbenzamide | 14 |
| N-[[[2-(Aminocarbonyl)phenyl]amino][(4-methoxybenzoyl)amino]methylene]-4-methylbenzamide | 10 |
| N-[[[3-(Aminocarbonyl)phenyl]amino][(4-methoxybenzoyl)amino]methylene]-4-methylbenzamide | 12 |
| N-[[[4-(Aminocarbonyl)phenyl]amino][(4-methylbenzoyl)amino]methylene]-3-methylbenzamide | 85 |
| N-[[[4-(Aminocarbonyl)phenyl]amino][(4-bromobenzoyl)amino]methylene]-4-methylbenzamide | 57 |
| N-[[[4-(Aminocarbonyl)phenyl]amino](benzoylamino)methylene]benzeneacetamide | 22 |
| N-[[[4-(Aminocarbonyl)phenyl]amino][(4-methoxybenzoyl)amino]methylene]-3-thiophenecarboxamide | 14 |
| N-[[[4-(Aminocarbonyl)phenyl]amino][(benzoylamino)methylene]-3-methylbenzamide | 33 |
| N-[[[3-(Aminocarbonyl)phenyl]amino][(4-methoxybenzoyl)amino]methylene]-2-thiophenecarboxamide | 19 |
| N-[[[3-(Aminocarbonyl)phenyl]amino](benzoylamino)methylene]-3-methylbenzamide | 15 |

The novel compounds of the present invention possess the ability to enhance neural function in warm-blooded animals affected by behavioral neurological problems, including the cognitive deterioration associated with decreased neural function which occurs with cerebral insufficiency, aging, dementia, and similar conditions.

A useful in vivo test that measures how effectively central nervous system-acting drugs enhance survival in a hypoxic environment, presumably by improving the ratio of energy supply to demand is known as the Hypoxic Survival Test. This test demonstrates the ability of the test compounds relative to a known parasympathomimetic agent physostigmine. This test shows the enhanced survival of test animals in a hypoxic environment after treatment with drug as compared to saline treated control animals without drug. Extensive testing has demonstrated that under conditions of 10% oxygen, only 5–20% of control mice (treated with saline) survive after 5 minutes, whereas 60–80% of the physostigmine treated mice survive. Drugs are tested by intraperitoneally injecting groups of mice 30 minutes prior to placing them in a hypoxic mixture and measuring survival. The rationale of this test is that drugs which enhance survival under hypoxic conditions without concomitant, depression or sedative side effects, may do so by enhancing energy metabolism, or by preserving normal brain function under conditions of reduced energy metabolism. Given the dependence of the brain on a constant supply of energy, drugs which have this property may have many far-reaching therapeutic indications, including recovery from stroke and closed head injury, as well as reducing the deleterious effects of the aging central nervous system. For example, in aged and senile demented patients, energy metabolism is known to be deficient, and is thought to contribute significantly to the neurochemical and neurophysiological dysfunctions of aging.

Groups of 20 Royal Hart mice (6 weeks of age) are injected intraperitoneally with test compound (1-200 mg/kg) 30 minutes prior to placing them in a hypoxic mixture (10% oxygen in 90% carbon dioxide) and measuring survival after 5 minutes.

A separate group of 20 mice is injected intraperitoneally with saline solution (0.01 cc/g of body weight) and processed as described above.

Still another group of 20 mice is injected intraperitoneally with 0.125 mg/kg of physostigmine and processed as described above.

Results of this test on representative compounds of the present invention are reported in Table II.

TABLE II

| Hypoxic Survival Test | | |
|---|---|---|
| Compound | Dose mg/kg | % Survivors |
| N,N'-[[[4-(Aminocarbonyl)phenyl]imino]-methylene]bis[benzamide] | 50 | 40 |
| | 100 | 62 |
| | 200 | 47 |
| N,N'-[[2-(Diethylamino)ethyl]carbonimidoyl]bis[4-(trifluoromethyl)benzamide] | 10 | 45 |
| | 50 | 70 |
| | 100 | 65 |
| | 200 | 85 |
| N,N'-[[4-(Aminocarbonyl)phenyl]carbonimidoyl]bis[3-methylbenzamide] | 50 | 40 |
| | 100 | 43 |
| N,N'-[[2-(Aminocarbonyl)phenyl]carbonimidoyl]bis[3-methylbenzamide] | 50 | 40 |
| | 100 | 48 |
| N-[[[4-(Aminocarbonyl)phenyl]amino]-(benzoylamino)methylene]-4-bromobenzamide | 10 | 42 |
| | 25 | 60 |
| | 100 | 43 |
| N-[[[4-(Aminocarbonyl)phenyl]amino]-(benzoylamino)methylene]tricyclo-[3.3.1.1$^{3,7}$]decane-1-carboxamide | 50 | 42 |
| N-[[[4-(Aminocarbonyl)phenyl]amino]-(benzoylamino)methylene]-3-bromobenzamide | 10 | 50 |
| N-[[[4-(Aminocarbonyl)phenyl]amino]-(benzolyamino)methylene]-3,4,5-trimethoxybenzamide | 10 | 50 |
| | 25 | 50 |
| N-[[[4-(Aminocarbonyl)phenyl]amino]-[(1-oxo-3-phenyl-2-propenyl)amino]-methylene]benzamide | 100 | 40 |
| N-[[[4-(Aminocarbonyl)phenyl]amino]-[4-methylbenzoyl)amino]methylene]-4-methoxybenzamide | 100 | 43 |
| N,N'-[[[4-(Sulfamoyl)benzyl]imino]-methylene]bis[benzamide] | 10 | 50 |
| | 100 | 35 |
| N-[[[4-(Aminocarbonyl)phenyl]amino]-[(4-methoxybenzoyl)amino]methylene]-4-(trifluoromethyl)benzamide | 50 | 55 |
| | 100 | 47 |
| N-[[[4-(Aminocarbonyl)phenyl]amino]-(benzoylamino)methylene]-2-thiophenecarboxamide | 10 | 50 |
| | 50 | 50 |
| N-[[[4-(Aminocarbonyl)phenyl]amino]-[(4-bromobenzoyl)amino]methylene]-4-fluorobenzamide | 25 | 40 |
| | 100 | 44 |
| N-[[[4-(Aminocarbonyl)phenyl]amino]-[(4-fluorobenzoyl)amino]methylene]-4-methoxybenzamide | 25 | 45 |
| | 50 | 60 |
| | 100 | 42 |
| N-[[[4-(Aminocarbonyl)phenyl]amino]-[(benzoylamino)methylene]-4-(trifluoromethyl)benzamide | 50 | 45 |
| N-[[[4-(Aminocarbonyl)phenyl]amino]- | 10 | 50 |

TABLE II-continued

| Hypoxic Survival Test | | |
|---|---|---|
| Compound | Dose mg/kg | % Survivors |
| [(4-methoxybenzoyl)amino]methylene]-3-methylbenzamide | 50 | 45 |
| | 100 | 50 |
| | 200 | 45 |
| N-[[[3-(Aminocarbonyl)phenyl]amino]-[(4-methoxybenzoyl)amino]methylene]-2-thiophenecarboxamide | 50 | 45 |
| | 100 | 45 |

Another in vivo test associated with decreased neural function in mammals is the Passive-Avoidance Anoxic-Induced-Amnesia Test. This test is used to determine the attenuation of anoxic induced amnesia in mice treated with drug, as compared to saline treated control animals with no drug.

A shock-motivated, single trial, step-through passive avoidance procedure is used. Groups of 25 Swiss-Webster, middle-aged mice (9 months of age) are placed singly in the front chamber of a 2-chamber box and are allowed to voluntarily cross into the rear chamber. As soon as the mouse enters the rear chamber, a door automatically traps the animal and a mild electric shock (0.4 mA for 4 seconds) is delivered to its feet. Following the foot shock, the mice are initially placed in an anoxic environment (0% oxygen) for 12 seconds, which quickly induces unconsciousness. They are then placed in a hypoxic environment (15% oxygen) for four minutes which prolongs the oxygen deprived state, maintaining unconsciousness. All testing is performed 24 hours later, and in all cases the mice appear fully recovered from the previous anoxic/hypoxic treatment. All test compounds are administered intraperitoneally at a dose of 10-200 mg/kg, 30 minutes prior to training and testing. Control animals are injected intraperitoneally only with saline at 0.01 cc/g of body weight.

The latency to enter the rear chamber is recorded for both training and testing. Presumably, the more the animal remembers being shocked, the greater it will inhibit going into the rear chamber and the higher will be its latency to re-enter. An improvement of 30% over saline control scores is considered active. The result of this test on a representative compound of the present invention appears in Table III.

TABLE III

| Passive Avoidance Anoxic Induced Amnesia Test | | |
|---|---|---|
| Compound | Dose mg/kg | % Improvement |
| N,N'-[[[4-(Aminocarbonyl)phenyl]-imino]methylene]bis[benzamide] | 50 | 50 |
| | 50 | 54 |

Certain of the novel compounds of the present invention have been found to be useful for meliorating anxiety in mammals when administered in amounts ranging from about 0.5 mg to about 100 mg/kg of body weight per day. A preferred dosage regimen for optimum results would be from about 10 mg to about 50 mg/kg of body weight per day, and such dosage units are employed that a total of from about 700 mg to about 3.5 g of the active compound for a subject of about 70 kg of body weight are administered in a 24 hour period.

Certain of the compounds of the present invention have been found to be useful as agents for the treatment of cognitive and related neural behavioral problems in mammals when administered in amounts ranging from about 5 mg to about 200 mg/kg of body weight per day.

A preferred dosage regimen for optimum results would be from about 10 mg to about 50 mg/kg of body weight per day and such dosage units are employed that a total of from about 700 mg to about 3.5 g of the active compound for a subject of about 70 kg of body weight are administered in a 24 hour period.

The hereinabove described dosage regimen for meliorating anxiety and treating neural behavioral problems in mammals may be adjusted to provide the optimum therapeutic response For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can a be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectabale use include sterile aqueous solutions or dispersions and sterile powders for the extemporaneous preparation of sterile injectable solutions or dispersions. In all cases, the form must be sterile and must be fluid to the extent that easy syringability exists It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following specific examples.

EXAMPLE 1

N-N′-Dibenzoylcarbamimidothioic acid, methyl ester

To a chilled (ice bath), stirred mixture of 367.6 g (1.32 moles) of 2-methyl-2-thiopseudourea sulfate and 1200 ml of pyridine was added 742.5 g (5.28 moles) of benzoyl chloride dropwise, over a 2 hour period while maintaining the reaction mixture temperature at less than 15° C. The mixture of crystals and liquid was stored for 16 hour at room temperature. Then the mixture was diluted with two liters of water and filtered to give 530 g of cream colored crystals This material was recrystallized from eight liters of acetonitrile and gave 300.6 g of 1,3-dibenzoyl-2-methyl-2-thiopseudourea as white crystals mp 144°–147° C.

The procedure described above and using the appropriately substituted benzoyl chloride was used to prepare the compounds listed in Table IV.

TABLE IV

N,N′-Bis[(monosubstituted)benzoyl]carbamimidothioic acid, methyl esters $$R-\underset{O}{\overset{O}{\|}}CCl + \left(\underset{H_2NC=NH}{\overset{SCH_3}{|}}\right)_2 \cdot H_2SO_4 \longrightarrow$$

$$R-\underset{\overset{\|}{O}}{C}-\underset{H}{N}-\underset{}{\overset{SCH_3}{\overset{|}{C}}}=N-\underset{\overset{\|}{O}}{C}-R$$

| Name | R | MP °C. |
|---|---|---|
| N,N′-Bis[4-(methoxy)benzoyl]carbamimidothioic acid, methyl ester | CH₃O—⟨phenyl⟩— | 161–162 |
| N,N′-Bis[3-(trifluoromethyl)benzoyl]carbamimidothioic acid, methyl ester | CF₃—⟨phenyl⟩— | 140–143 |
| N,N′-Bis[4-(trifluoromethyl)benzoyl]carbamimidothioic acid, methyl ester | CF₃—⟨phenyl⟩— | 168–171 |
| N,N′-Bis(3-methylbenzoly)carbamimidothioic acid, methyl ester | CH₃—⟨phenyl⟩— | 88–90 |

EXAMPLE 2

N-(Aminothioxomethyl)benzamide

To a two-liter-round-bottomed flask fitted with an overhead stirrer, addition funnel and a condenser was added 400 ml of acetone and 85.0 g (1.12 moles) of ammonium thiocyanate. To this solution was added 140.6 g (1.00 moles) of benzoyl chloride. The resultant slurry was heated at reflux for 15 minutes and then the heat was removed and 200 ml of concentrated ammonium hydroxide was added at a rate to maintain reflux. The reaction mixture was heated at reflux for an additional 15 minutes and then cooled to room temperature. This mixture was added to 6 liters of water, and the resulting precipitate was collected by filtration and washed with 2 liters of water, then air dried and recrystallized from 1.5 liters of ethanol to give 98.5 g of the desired product as a white solid, mp 170°–171° C.

The procedure described hereinabove and using the appropriately substituted acid chloride was used to prepare the compounds listed in Table V.

TABLE V

N-(Aminothioxomethyl)aryl and heteroaryl amides $$R_1-\overset{O}{\underset{\|}{C}}Cl + NH_4SCN \xrightarrow[(2)\ NH_4OH,\ \Delta]{(1)\ Acetone,\ \Delta} R_1-\overset{O}{\underset{\|}{C}}-\underset{H}{N}-\overset{S}{\underset{\|}{C}}-NH_2$$

| Name | $R_1$ | MP °C. |
|---|---|---|
| N-(Aminothioxomethyl)-4-fluorobenzamide | F—⌬— | 190–192 |
| N-(Aminothioxomethyl)-4-methoxybenzamide | CH₃O—⌬— | 116–118 |
| N-(Aminothioxomethyl)-4-methylbenzamide | H₃C—⌬— | 220–221 |
| N-(Aminothioxomethyl)-2-furancarboxamide | (furan) | 179–180 |

TABLE V-continued

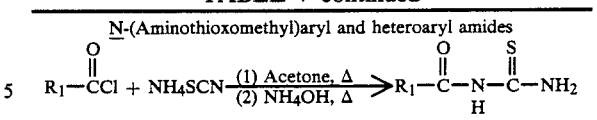

| Name | $R_1$ | MP °C. |
|---|---|---|
| (E)N-(aminothioxomethyl)-3-phenyl-2-propenamide | Ph—CH=CH— | 222–223 |
| N-(Aminothioxomethyl)-4-chlorobenzamide | Cl—⌬— | 215–216 |
| N-(Aminothioxomethyl)-3-methylbenzamide | H₃C—⌬— | 154–156 |

EXAMPLE 3

N-Benzoylcarbamimidothioic acid, methyl ester monohydridodide

To an 18.0 g (0.1 mole) amount of N-(aminothioxomethyl)benzamide in 300 ml of acetone was added 15.0 ml of methyl iodide (34.2 g, 0.24 mole). The mixture was heated as reflux and after about 5 minutes a solid precipitate formed. Refluxing was continued for 2 hours, then the hot reaction mixture was filtered to collect the precipitate. The precipitate was washed with two 50 ml portions of acetone, then air dried to give 28.9 g of the product as a white solid, mp 189°–190° C. (dec.).

The procedure described hereinabove was used to prepare the compounds listed in Table VI.

TABLE VI

N-(Aroyl or heteroaroyl)carbamimidothioic acid, methyl ester, momohydroidides $$R_1-\overset{O}{\underset{\|}{C}}-\underset{H}{N}-\overset{S}{\underset{\|}{C}}-NH_2 + CH_3I \xrightarrow[\text{or ethyl acetate}]{\text{Acetone}} R_1-\overset{O}{\underset{\|}{C}}-N=\overset{SCH_3}{\underset{|}{C}}-NH_2 \cdot HI$$

| Name | $R_1$ | MP °C. | Reaction Solvent |
|---|---|---|---|
| N-(4-Methoxybenzoyl)carbamimidothioic acid, methyl ester, monohydriodide | H₃CO—⌬— | 182–184 (dec.)* | Acetone |
| N-(4-Methylbenzoyl)carbamimidothioic acid, methyl ester, monohydriodide | H₃C—⌬— | 199–201 (dec.) | Acetone |
| N-(2-Furanylcarbonyl)carbamimidothioic acid, methly ester, monohydriodide | (furan) | 189–190 (dec.) | Acetone |
| N-(1-Oxo-3-phenyl-2-propenyl)carbaminidothioic acid, methyl ester, monohydriodide | Ph—CH=CH— | 210 (dec.) | Acetone |

TABLE VI-continued

N-(Aroyl or heteroaroyl)carbamimidothioic acid, methyl ester, momohydroidides $$R_1-\overset{\overset{O}{\|}}{C}-\underset{H}{N}-\overset{\overset{S}{\|}}{C}-NH_2 + CH_3I \xrightarrow[\text{or ethyl acetate}]{\text{Acetone}} R_1-\overset{\overset{O}{\|}}{C}-N=\overset{\overset{SCH_3}{|}}{C}-NH_2.HI$$

| Name | $R_1$ | MP °C. | Reaction Solvent |
|---|---|---|---|
| N-(4-Chlorobenzoyl)carbamimidothioic acid, methyl ester, monohydriodide | CL—C₆H₄— | 187–188 (dec.) | Acetone |
| N-(4-Fluorobenzoyl)carbamimidothioic acid, methyl ester, monohydriodide | F—C₆H₄— | 170–171 | Ethyl acetate |
| N-(3-Methylbenzolyl)carbamimidothioic acid, methyl ester, monohydriodide | H₃C—C₆H₄— | 171–174 (dec.) | Acetone |

*Recrystallized from acetonitrile

EXAMPLE 4

N-Benzoyl-N'-(3-bromobenzoyl)carbamimidothioic acid, methyl ester

To a stirred slurry of 16.1 g (0.05 mole) of N-benzoylcarbamimidothioic acid, methyl ester monohydriodide in 150 ml of pyridine was added 10.97 g (0.05 mole) of 3-bromobenzoyl chloride. The resulting dark red-brown mixture slowly lightened to a yellow solution then a precipitate formed. Stirring was continued for 4 hours, then the mixture was quenched in 1.5 liters of water and stirred for 30 minutes. The precipitate was collected by filtration, washed with four 250-ml-portions of water, air dried, then dried in vacuo over phosphorus pentoxide to give 16.55 g of the product of this example as a white solid, mp 145°–146° C.

The procedure described hereinabove and using a previously described substituted-N-benzoylcarbamimidothioic acid, methyl ester monohydriodide with an appropriately substituted acid chloride gave the unsymmetrically substituted N,N'-diacylcarbamimidothioic acid, methyl esters listed in Table VII.

TABLE VII

N,N'-Unsymmetrical carbamimidothioic acid, methyl esters $$R_1-\overset{\overset{O}{\|}}{C}-N=\overset{\overset{SCH_3}{|}}{C}-NH_2.HI + R-\overset{\overset{O}{\|}}{C}-Cl \xrightarrow{\text{pyridine}} R_1-\overset{\overset{O}{\|}}{C}-N=\overset{\overset{SCH_3}{|}}{C}-\underset{H}{N}-\overset{\overset{O}{\|}}{C}-R$$

| Name | R | $R_1$ | MP °C. |
|---|---|---|---|
| N-Benzoyl-N'-(4-bromobenzoyl)carbamimidothioic acid, methyl ester | —C₆H₄—Br | —C₆H₅ | 146–147 |
| N-Benzoyl-N'-(tricyclo[3.3.1-1³,⁷]dec-1-ylcarbonyl)carbamimidothioic acid, methyl ester | adamantyl | —C₆H₅ | 143–145 |
| N-Benzoyl-N'-(4-methoxybenzoyl)carbamimidothioic acid, methyl ester | —C₆H₅ | CH₃O—C₆H₄— | 145–146 |
| N-Benzoyl-N'-(4-fluorobenzyl)carbamimidothioic acid, methyl ester | —C₆H₅ | F—C₆H₄— | 177–178 |

TABLE VII-continued

N,N'-Unsymmetrical carbamimidothioic acid, methyl esters $$R_1-\overset{O}{\underset{}{C}}-N=\overset{SCH_3}{\underset{}{C}}-NH_2 \cdot HI + R-\overset{O}{\underset{}{C}}-Cl \xrightarrow{\text{pyridine}} R_1-\overset{O}{\underset{}{C}}-N=\overset{SCH_3}{\underset{}{C}}-\underset{H}{N}-\overset{O}{\underset{}{C}}-R$$

| Name | R | R₁ | MP °C. |
|---|---|---|---|
| N-Benzoyl-N'-(4-cyanobenzoyl)carbamimidothioic acid, methyl ester | 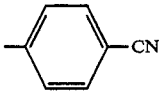 | 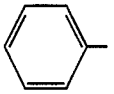 | 199–200 |
| N-Benzoyl-N'-(1-oxo-3-phenyl-2-propenyl)carbamimidothioic acid, methyl ester | 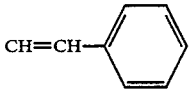 | 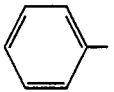 | 133–134 |
| N-(4-Methoxybenzoyl)-N'-(4-methylbenzoyl)carbamimidothioic acid, methyl ester | 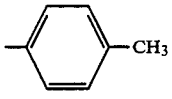 | 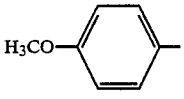 | 134–137 (dec.) |
| N-(4-Methoxybenzoyl)-N'-[4-(trifluoromethyl)benzoyl]carbamimidothioic acid, methyl ester | 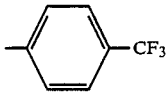 | 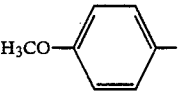 | 162–164 |
| N-Benzoyl-N'-(3,4,5-trimethoxybenzoyl)carbamimidothioic acid, methyl ester | 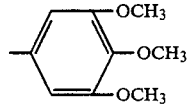 | 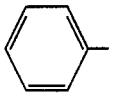 | 145–146 |
| N-(4-Bromobenzoyl)-N'-(4-methylbenzoyl)carbamimidothioic acid, methyl ester | 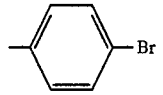 | 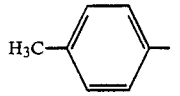 | 146–147 |
| N-(4-Bromobenzoyl)-N'-(4-fluorobenzoyl)carbamimidothioic acid, methyl ester | 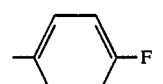 | 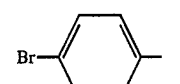 | 162–163 |
| N-(4-Fluorobenzoyl)-N'-(4-methoxybenzoyl)carbamimidothioic acid, methyl ester | 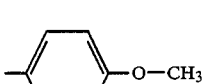 | 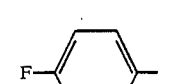 | 175–176 |
| N-(4-Methoxybenzoyl)-N'-(3-methylbenzoyl)carbamimidothioic acid, methyl ester |  |  | 145–147 |
| N-Benzoyl-N'-(phenoxyacetyl)carbamimidothioic acid, methyl ester | 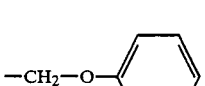 | 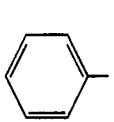 | 149–150 |

TABLE VII-continued

N,N'-Unsymmetrical carbamimidothioic acid, methyl esters $$R_1-\overset{O}{\underset{}{C}}-N=\overset{SCH_3}{\underset{}{C}}-NH_2 \cdot HI + R-\overset{O}{\underset{}{C}}-Cl \xrightarrow{\text{pyridine}} R_1-\overset{O}{\underset{}{C}}-N=\overset{SCH_3}{\underset{H}{C}}-N-\overset{O}{\underset{}{C}}-R$$

| Name | R | R₁ | MP °C. |
|---|---|---|---|
| N-Benzoyl-N'-(2-thienylcarbonyl)-carbamimidothioic acid, methyl ester |  | 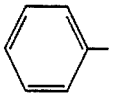 | 159–160 |
| N-Acetyl-N'-benzoyl)carbamimidothioic acid, methyl ester | —CH₃ | 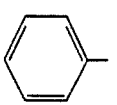 | 142–144 |
| N-Benzoyl-N'-[4-(trifluoromethbenzoyl]carbamimidothioic acid, methyl ester | 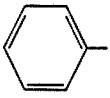 | 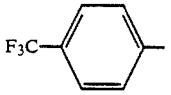 | 131–132 |
| N-(4-Bromobenzoyl)-N'-(4-chlorobenzoyl)-carbamimidothioic acid, methyl ester | 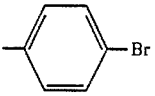 | 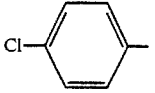 | 175–176 |
| N-(4-Fluorobenzoyl)-N'-(tricyclo[3.3.1.1³·⁷]-dec-1-ylcarbonyl)carbamimidothioic acid, methyl ester | 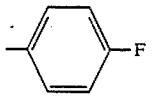 |  | 196–197 |
| N-Benzoyl-N'-[2-(trifluoromethyl)benzoyl]carbamimidothioic acid, methyl ester |  | 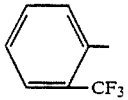 | 124–125 |
| N-Benzoyl-N'-(3-methylbenzoyl)-carbamimidothioic acid, methyl ester | 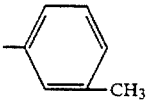 | 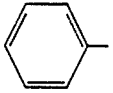 | 103–105 |
| N-(4-Methoxybenzoyl)-N'-(2-thienylcarbonyl)carbamimidothioic acid, methyl ester | 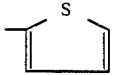 | 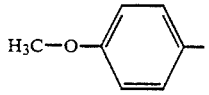 | 180–182 |
| N-Benzoyl-N'-(phenylacetyl)-carbamimidothioic acid, methyl ester | —CH₂—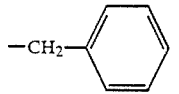 | 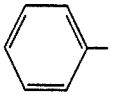 | 107–108 |
| N-Benzoyl-N'-(1-oxo-3-phenyl-propyl)carbamimidothioic acid, methyl ester | —CH₂CH₂—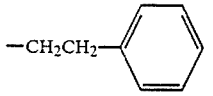 | 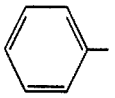 | 92–93 |

TABLE VII-continued

N,N'-Unsymmetrical carbamimidothioic acid, methyl esters $$R_1-\overset{O}{\overset{\|}{C}}-N=\overset{SCH_3}{\overset{|}{C}}-NH_2\cdot HI + R-\overset{O}{\overset{\|}{C}}-Cl \xrightarrow{pyridine} R_1-\overset{O}{\overset{\|}{C}}-N=\overset{SCH_3}{\overset{|}{C}}-\underset{H}{N}-\overset{O}{\overset{\|}{C}}-R$$

| Name | R | R₁ | MP °C. |
|---|---|---|---|
| N-(3-Methylbenzoyl)-N'-(4-methylbenzoyl)carbamimidothioic acid, methyl ester | 4-methylphenyl | 3-methylphenyl | 114–119 (dec.) |
| N-Benzoyl-N'-(3-fluorobenzoyl)-carbamimidothioic acid, methyl ester | 3-fluorophenyl | phenyl | 169–169.5 |
| N-Benzoyl-N'-(3,5-dimethoxybenzoyl)carbamimidothioic acid, methyl ester | 3,5-dimethoxyphenyl | phenyl | 144–145 |
| N-Benzoyl-N'-(3-chlorobenzoyl)-carbamimidothioic acid, methyl ester | 3-chlorophenyl | phenyl | 146 |
| N-(3-Chlorobenzoyl)-N'-(1-oxo-3-phenyl-2-propenyl)carbamimidothioic acid, methyl ester | 3-chlorophenyl | phenyl—CH=CH— | 150–151 |
| N-(3-Fluorobenzoyl)-N'-(1-oxo-3-phenyl-2-propenyl)carbamimidothioic acid, methyl ester | 3-fluorophenyl | phenyl—CH=CH— | 159–160 |
| N-(3-Chlorobenzoyl)-N'-(4-fluorobenzoyl)carbamimidothioic acid, methyl ester | 3-chlorophenyl | 4-fluorophenyl | 139–140 |
| N-(3-Fluorobenzoyl)-N'-(4-fluorobenzoyl)carbamimidothioic acid, methyl ester | 3-fluorophenyl | 4-fluorophenyl | 171–172 |
| N-Benzoyl-N'-(3-cyclohexen-1-ylcarbonyl)carbamimidothioic acid, methyl ester | 3-cyclohexen-1-yl | phenyl | 99–100 |
| N-Benzoyl-N'-(2,2-dimethyl-1-oxopropyl)carbamimidothioic acid, methyl ester | —C(CH₃)₃ | phenyl | 91–92 |

TABLE VII-continued

N,N'-Unsymmetrical carbamimidothioic acid, methyl esters $$R_1-\overset{O}{\underset{\|}{C}}-N=\overset{SCH_3}{\underset{|}{C}}-NH_2\cdot HI + R-\overset{O}{\underset{\|}{C}}-Cl \xrightarrow{\text{pyridine}} R_1-\overset{O}{\underset{\|}{C}}-N=\overset{SCH_3}{\underset{|}{C}}-\underset{H}{N}-\overset{O}{\underset{\|}{C}}-R$$

| Name | R | R₁ | MP °C. |
|---|---|---|---|
| N-Benzoyl-N'-(1-oxopentyl)carbamimidothioic acid, methyl ester | —CH₂CH₂CH₂CH₃ |  | 66–67 |
| N-Benzoyl-N'-[4-(1,1-dimethylethyl)benzoyl]carbamimidothioic acid, methyl ester | 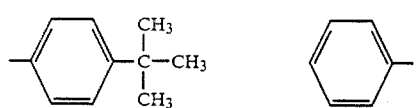 |  | 120.5–121.5 |
| N-Benzoyl-N'-([1,1'-biphenyl]-4-ylcarbonyl)carbamimidothioic acid, methyl | 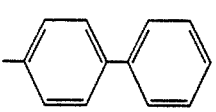 |  | 167–168 |
| N-Benzoyl-N'-(3-nitrobenzoyl)carbamimidothioic acid, methyl ester | 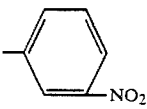 |  | 178.5–179.5 |
| N-Benzoyl-N'-(1-oxodecyl)carbamimidothioic acid, methyl ester | —(CH₂)₈CH₃ |  | 43–44 |
| N-Benzoyl-N'-(cyclobutylcarbonyl)carbamimidothioic acid, methyl ester |  |  | 94.5–95.5 |
| N-Benzoyl-N'-(cyclopropylcarbonyl)carbamimidothioic acid, methyl ester |  |  | 113–115 |

EXAMPLE 5

N,N'-[[[4-(Aminocarbonyl)phenyl]imino]methylene]-bis[benzamide]

A stirred mixture of 89.5 g (0.3 mole) of N,N'-dibenzoylcarbamimidothio acid, methyl ester (Example 1), 40.8 g (0.3 mole) of 4-aminobenzamide and three liters of isopropyl alcohol was heated under reflux for 24 hours. The evolution of methanethiol was monitored with lead acetate paper. The reaction mixture was cooled and filtered to collect a white crystalline solid. The solid was washed with one liter of hot acetonitrile, then dried in vacuo to give 94.8 g of the desired product as white crystals, mp 276°–278° C. (dec.).

In a like manner when 4-aminobenzamide is replaced in the procedure of Example 5 with 4-(methylamino)benzamide, 4-(ethylamino)benzamide, 4-(n-hexylamino)benzamide, 4-(cyclohexylamino)benzamide or 4-(2-cyclohexylethylamino)benzamide the respective products obtained are: N,N'-[[[4-(aminocarbonyl)phenyl]methylamino]methylidyne]bisbenzamide; N,N'-[[[4-(aminocarbonyl)phenyl]ethylamino]methylidyne]bisbenzamide; N,N'-[[[4-(aminocarbonyl)phenyl]n-hexylamino]methylidyne]bisbenzamide; N,N'-[[[4-(aminocarbonyl)phenyl]cyclohexylamino]methylidyne]bisbenzamide; and N,N'-[[[4-(aminocarbonyl)phenyl]-2-cyclohexylethyl]amino]benzamide.

Example 6

N-[[[4-(Aminocarbonyl)phenyl]amino](benzoylamino)methylene]-3-bromobenzamide

A mixture of 7.55 g (0.02 mole) of N-benzoyl-N-'-(3-bromobenzoyl)carbamimidothioic acid, methyl ester, 2.72 g (0.02 mole) of 4-aminobenzamide and 250 ml of isopropyl alcohol was heated at reflux for 48 hours resulting in precipitation of a solid. The solid was collected by filtration and washed with two 50 ml portions of hot isopropyl alcohol to give 6.35 g of the desired product as a white solid, mp 282°–283° C.

EXAMPLES 7–40

The compounds of Examples 7–40 were prepared in the manner described in Examples 5 and 6, wherein 4-aminobenzamide was reacted with the appropriately substituted unsymmetrical N,N'-diacylcarbamimidothioic acid, methyl ester. The compounds of Examples 7-40 are listed in Table VIII.

TABLE VIII

Symmetrical and Unsymmetrical [[4-(aminocarbonyl)phenyl]amino]benzamides $$R_1-\overset{O}{\overset{\|}{C}}-N=\overset{S-CH_3}{\underset{H}{\overset{|}{C}}}-N-\overset{O}{\overset{\|}{C}}-R + H_2N-\underset{}{\underset{}{\bigcirc}}-CONH_2 \xrightarrow[\text{Isopropyl alcohol}]{\Delta} R_1-\overset{O}{\overset{\|}{C}}-N=\overset{HN-\bigcirc-\overset{O}{\overset{\|}{C}}-NH_2}{\underset{H}{\overset{|}{C}}}-N-\overset{O}{\overset{\|}{C}}-R$$

| Ex. | Name | R | R₁ | Reaction Time | MP °C. | Description and Comments |
|---|---|---|---|---|---|---|
| 7 | N,N'-[[4-(Aminocarbonyl)-phenyl]carbonimidoyl]bis-[3-methylbenzamide] | 3-CH₃-phenyl | 3-CH₃-phenyl | 1 hour | 252-256 | off-white crystals |
| 8 | N-[[[4-(Aminocarbonyl)-phenyl]amino](benzoyl-amino)methylene]-4-bromo-benzamide | phenyl | 4-Br-phenyl | 24 hours | 291-292 | white solid |
| 9 | N-[[[4-(Aminocarbonyl)-phenyl]amino](benzoyl-amino)methylene]tricyclo-[3.3.1.1³·⁷]decane-1-carboxamide | phenyl | adamantyl | 18 hours | 282-283 | white solid |
| 10 | N-[[[4-(Aminocarbonyl)-phenyl]amino](benzoyl-amino)methylene]-4-methoxybenzamide | phenyl | 4-CH₃O-phenyl | 24 hours | 272-273 | white solid |
| 11 | N-[[[4-(Aminocarbonyl)-phenyl]amino](benzoyl-amino)methylene]-4-fluorobenzamide | phenyl | 4-F-phenyl | 7 days | 288-289 | white solid |
| 12 | N-[[[4-(Aminocarbonyl)-phenyl]amino](benzoyl-amino)methylene]-3,4,5-trimethoxybenzamide | phenyl | 3,4,5-(CH₃O)₃-phenyl | 48 hours | 272-273 | white solid |
| 13 | N[[[4-(Aminocarbonyl)-phenyl]amino][1-oxo-3-phenyl-2-propenyl)amino]-methylene]benzamide | —CH=CH—phenyl | phenyl | 48 hours | 273-274 | white solid |
| 14 | N-[[[4-(Aminocarbonyl)-phenyl]amino](benzoyl-amino)methylene]-4-cyano-benzamide | phenyl | 4-CN-phenyl | 48 hours | 267-268 | white solid |
| 15 | N-[[[4-(Aminocarbonyl)-phenyl]amino][4-methyl-benzoyl)amino]methylene]-4-methoxybenzamide | 4-CH₃-phenyl | 4-CH₃O-phenyl | 8 hours | 282-285 (dec.) | white crystals |

TABLE VIII-continued

Symmetrical and Unsymmetrical [[4-(aminocarbonyl)phenyl]amino]benzamides

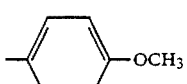

| Ex. | Name | R | $R_1$ | Reaction Time | MP °C. | Description and Comments |
|---|---|---|---|---|---|---|
| 16 | N-[[[4-(Aminocarbonyl)-phenyl]amino][(4-methoxy-benzoyl)amino]methylene]-4-(trifluoromethyl)-benzamide | 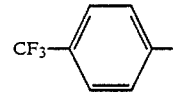 -OCH₃ | CF₃- 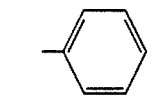 | 8 hours | 281–282 (dec.) | white crystals |
| 17 | N-[[[4-(Aminocarbonyl)-phenyl]amino](benzoyl-amino)methylene]-2-thio-phenecarboxamide |  | 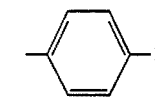 | 18 hours | 282–283 | white solid |
| 18 | N-[[[4-(Aminocarbonyl)-phenyl]amino][(4-fluoro-benzoyl)amino]methylene]-4-methoxybenzamide | 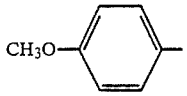 -F | CH₃O- 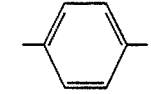 | 7 days | 285–286 | white solid |
| 19 | N-[[[4-(Aminocarbonyl)-phenyl]amino][(4-bromo-benzoyl)amino]methylene]-4-fluorobenzamide | 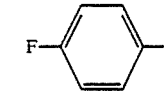 -Br | F- 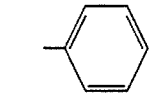 | 7 days | 289–290 | white solid |
| 20 | N-[[[4-(Aminocarbonyl)-phenyl]amino][benzoyl-amino]methylene]-4-(tri-fluoromethyl)benzamide | 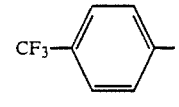 | CF₃- 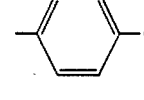 | 24 hours | 290–291 | white solid |
| 21 | N-[[[4-(Aminocarbonyl)-phenyl]amino][(4-methyl-benzoyl)amino]methylene]-3-methylbenzamide | 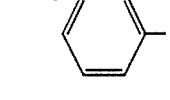 -CH₃ | 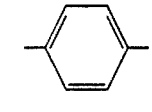 CH₃ | 14 hours | 268–269 (dec.) | white crystals |
| 22 | N-[[[4-(Aminocarbonyl)-phenyl]amino][(4-bromo-benzoyl)amino]methylene]-4-methylbenzamide | 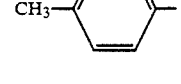 -Br | CH₃- 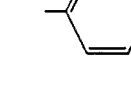 | 4 days | 294–294.5 | white solid recrystallized from dimethyl sulphoxide |
| 23 | N-[[[4-(Aminocarbonyl)-phenyl]amino](benzoyl-amino)methylene]benzene-acetamide | 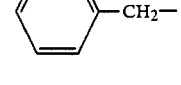 | 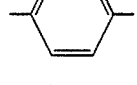 -CH₂- | 24 hours | 231–232 | yellow solid |
| 24 | N-[[[4-(Aminocarbonyl)-phenyl]amino][4-methoxy-benzoyl)amino]methylene]-2-thiophene carboxamide | 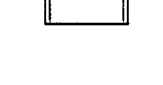 -OCH₃ | 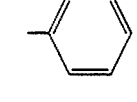 | 14 hours | 268–270 (dec.) | white crystals |
| 25 | N[[[4-(Aminocarbonyl)-phenyl]amino](benzoyl-amino)methylene]-3-methylbenzamide |  -CH₃ |  | 7 hours | 281–283 (dec.) | white crystals |

TABLE VIII-continued
Symmetrical and Unsymmetrical [[4-(aminocarbonyl)phenyl]amino]benzamides

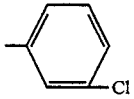

| Ex. | Name | R | R₁ | Reaction Time | MP °C. | Description and Comments |
|---|---|---|---|---|---|---|
| 26 | N-[[[4-(Aminocarbonyl)-phenyl]amino](benzoyl-amino)methylene]-3-chlorobenzamide | 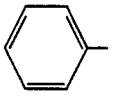 | 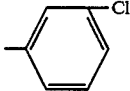 | 24 hours | 272-272.5 | white solid |
| 27 | N-[[[4-(Aminocarbonyl)-phenyl]amino][(3-chloro-benzoyl)amino]methylene]-4-fluorobenzamide | 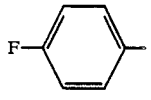 | 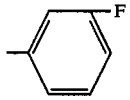 | 24 hours | 269-270 | white solid |
| 28 | N-[[[4-(Aminocarbonyl)-phenyl]amino](4-fluoro-benzoyl)amino]methylene]-3-fluorobenzamide | 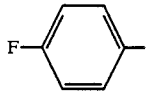 | 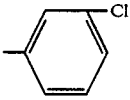 | 24 hours | 291 | white solid |
| 29 | N-[[[4-(Aminocarbonyl)-phenyl]amino][(1-oxo-3-phenyl-2-propenyl)amino]-methylene]-3-chlorobenz-amide | 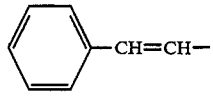 | 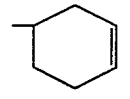 | 48 hours | 278.5-279.5 | white solid |
| 30 | N-[[[4-(Aminocarbonyl)-phenyl]amino][(3-cyclo-hexan-1-ylcarbonyl)-amino]methylene]benzamide | 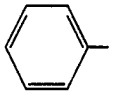 | 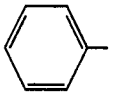 | 24 hours | 256.5-258 | white solid |
| 31 | N-[[[4-(Aminocarbonyl)-phenyl]amino][(1-oxo-pentyl)amino]methylene]-benzamide | —CH₂CH₂CH₂CH₃ | 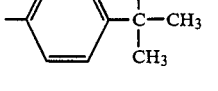 | 24 hours | 247 | white solid |
| 32 | N-[[[4-(Aminocarbonyl)-phenyl]amino](benzoyl-amino)methylene]-4-(1,1-dimethylethyl)benzamide | 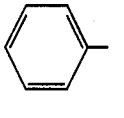 | 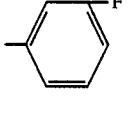 | 24 hours | 253-256 | white solid |
| 33 | N-[[[4-(Aminocarbonyl)-phenyl]amino][(1-oxo-3-phenyl-2-propenyl)amino]-methylene]-3-fluorobenz-amide | 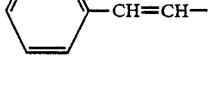 | 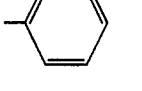 | 48 hours | 272.5-275 | white solid |
| 34 | N-[[[4-(Aminocarbonyl)-phenyl]amino](benzoyl-amino)methylene]-3-nitrobenzamide | 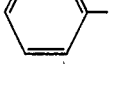 |  | 24 hours | 283-284 | pale yellow solid |
| 35 | N-[[[4-(Aminocarbonyl)-phenyl]amino][(cyclo-butylcarbonyl)amino]-methylene]benzamide | 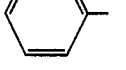 | | 24 hours | 242-243 | white solid |

TABLE VIII-continued
Symmetrical and Unsymmetrical [[4-(aminocarbonyl)phenyl]amino]benzamides

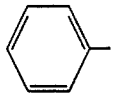

| Ex. | Name | R | R₁ | Reaction Time | MP °C. | Description and Comments |
|---|---|---|---|---|---|---|
| 36 | N-[[[4-(Aminocarbonyl)-phenyl]amino][(1-oxo-decyl)amino)amino]methylene]-benzamide | —(CH₂)₈CH₃ | phenyl | 24 hours | 209–211 | white solid |
| 37 | N-[[[4-(Aminocarbonyl)-phenyl]amino]](cyclo-propylcarbonyl)amino]-methylene]benzamide | cyclopropyl | phenyl | 24 hours | 250–251 | white solid |
| 38 | N-[[[4-(Aminocarbonyl)-phenyl]amino][(2,2-di-methyl-1-oxopropyl)-amino]methylene]benzamide | —C(CH₃)₃ | phenyl | 24 hours | 162–164 | white solid |
| 39 | N-[[[4-(Aminocarbonyl)-phenyl]amino](benzoyl-amino)methylene]-3,5-di-methoxybenzamide | 4-methoxyphenyl | phenyl | 24 hours | 261–264 | white solid |
| 40 | N-[[[4-(Aminocarbonyl)-phenyl]amino][(4-methoxy-benzoyl)amino]methylene]-methylbenzamide | 4-methoxyphenyl | 4-methylphenyl | 7 hours | 258–259 | white crystals |

EXAMPLE 41

N,N'-[[2-(Diethylaminoethyl]carbonimidoyl]bis[4-(tri-fluoromethyl)benzamide

A mixture of 7.0 g of 2-ethyl-2-thiopseudourea hydrobromide and 200 ml of pyridine was stirred at a temperature below 10° C. as 17.6 g of 4-trifluoromethylbenzoyl chloride was added over a 15 minute period. Then the solution was stirred at 4° C. for 16 hours. The solution was poured into one liter of water and the resulting precipitate was collected, washed with water and air dried. The precipitate was recrystallized from 200 ml of ethanol plus 150 ml of N,N-dimethylformamide at the boil, clarified hot with activated charcoal and filtered. The filtrate was cooled at −10° C., the precipitate was collected, washed with 100 ml of ethanol, air dried, then dried in vacuo at 60° C. and gave 9.6 g of 2-ethyl-2-thio-1,3-bis(α,α,α-trifluoro-p-toluoyl)-pseudourea, mp 173°–174° C.

A mixture of 6.0 g of the preceding product and 1.65 g of N,N-diethylethylenediamine in 75 ml of ethanol was stirred at reflux for 90 minutes then 75 ml of water was added and the solution was cooled at −10° C. in an ice bath. The resulting precipitate was collected, washed with 30 ml 1:2 aqueous ethanol and air dried. The product was recrystallized from isopropyl alcohol:water (2:1), collected, washed with isopropyl alcohol:water (1:1) and air dried to give 2.7 g of the product of the example as a white solid, mp 89°–91° C.

EXAMPLE 42

N,N'-[[[4-(Aminocarbonyl)phenyl]imino]methylene]-bis[benzamide]

(A) A mixture of 3.22 g of N-benzoylcarbamimidothioic acid, methyl ester, monohydriodide (Ex. 3), 1.36 g of 4-aminobenzamide and 150 ml of isopropyl alcohol was heated and maintained at reflux for 48 hours. The mixture gradually thickened and the solid that formed was collected by filtration. The solid was washed with 100 ml of hot isopropyl alcohol, then air dried to give 2.05 g of product, as the monohydriodide, mp 249°–250° C. (dec.). When this material was treated with aqueous sodium bicarbonate for hours the free base was isolated as N-[[[4-(aminocarbonyl)phenyl]amino]iminomethyl]-benzamide.

(B) To a slurry of 4.1 g of the preceding compound (prepared as described above) in 50.0 ml of pyridine was added 1.4 g of benzoyl chloride. The reaction mixture was stirred for 5 hours, then quenched into 500 ml of water. The precipitated product was collected, washed with 100 ml of water and air dried to give a pale yellow solid. The solid was recrystallized from dimethyl sulphoxide and gave 1.47 g of the product of the example as a white solid, mp 278°-279° C. (dec.).

EXAMPLE 43

N-[[-[4-(Aminocarbonyl)phenyl]amino]-(benzoylamino)methylene]-3-pyridinecarboxamide ]amino](benzoylamino)methylene]-3-pyridinecarboxamide.

EXAMPLES 44–46

The procedures described in Examples 5 and 6 were used to prepare the compounds of Examples 45–46 which are listed in Table IX.

TABLE IX

Symmetrical [[2-(Aminocarbonyl)phenyl]amino]benzamides

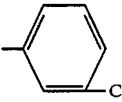

| Ex. | Name | R | $R_1$ | Reaction Time | MP °C. | Description and Comments |
|---|---|---|---|---|---|---|
| 44 | N,N'-[[2-(Aminocarbonyl)phenyl]carbonimidoyl]bis-[3-methylbenzamide] |  | 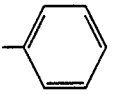 | 5 hours | 221–225 | gray crystals |
| 45 | N,N'-[[2-(Aminocarbonyl)phenyl]carbonimidoyl]bis-[benzamide] | 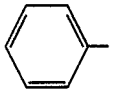 | 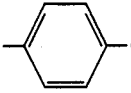 | 5 hours | 234–236 | gray crystals |
| 46 | N-[[[2-(Aminocarbonyl)phenyl]amino][(4-methoxybenzoyl)amino]methylene]-4-methylbenzamide | 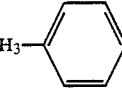 |  | 8 hours | 231–232 (dec.) | off-white crystals |

In a like manner, following the procedure of Example 42, nicotinoyl chloride is reacted with N-[[[4-(aminocarbonyl)phenyl]amino]iminomethyl]benzamide in pyridine to give N-[[[4-(aminocarbonyl)phenyl-

EXAMPLES 47–50

The procedures described in Examples 5 and 6 were used to prepare the compounds of Examples 47–50 which are listed in Table X.

TABLE X

Symmetrical and Unsymmetrical [[3-(Aminocarbonyl)phenyl]amino]benzamides

| Ex. | Name | R | $R_1$ | Reaction Time | MP °C. | Description and Comments |
|---|---|---|---|---|---|---|
| 47 | N,N'-[[3-(Aminocarbonyl)phenyl]carbonimidoyl]bis-[3-methylbenzamide] | 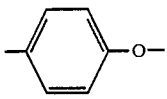 | 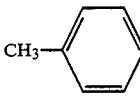 | 5 hours | 215–218 (dec.) | white crystals |
| 48 | N-[[[3-(Aminocarbonyl)phenyl]amino][(4-methoxybenzoyl)amino]methylene]-4-methylbenzamide | —⟨⟩—O—CH₃ | CH₃—⟨⟩— | 8 hours | 209–211 (dec.) | white crystals |

TABLE X-continued
Symmetrical and Unsymmetrical [[3-(Aminocarbonyl)phenyl]amino]benzamides

| Ex. | Name | R | $R_1$ | Reaction Time | MP °C. | Description and Comments |
|---|---|---|---|---|---|---|
| 49 | N-[[[3-(Aminocarbonyl)phenyl]amino][(4-methoxybenzoyl)amino]methylene]-2-thiophenecarboxamide | 4-methoxyphenyl | 2-thienyl | 7 hours | 235–237 (dec.) | white crystals |
| 50 | N-[[[3-(Aminocarbonyl)phenyl]amino](benzoylamino)methylene]-3-methylbenzamide | phenyl | 3-methylphenyl | 7 hours | 182–185 | white crystals |

EXAMPLE 51

N,N'-Dibenzoylcarbamimidoic acid, methyl ester

To a chilled (ice bath), stirred mixture of 2.50 g. of O-methylisourea hydrogen sulfate and 100 ml. of pyridine was added 78.7 g. of benzoyl chloride dropwise, over a 2 hour period while maintaining the reaction mixture temperature at less than 15° C. The mixture of crystals and liquid was stored for 16 hours at room temperature. Then the mixture diluted with water filtered to give 8.0 g. of N,N'-dibenzoylcarbamimidoic acid, methyl ester as colorless crystals, mp 139°–141° C.

EXAMPLE 52

N,N'-[[[(Aminocarbonyl)phenyl]imino]methylene]bis[benzamide]

A mixture of 4.0 g of N,N'-dibenzoylcarbamimidoic acid, methyl ester, 1.8 g. of 4-aminobenzamide and 100 ml of isopropyl alcohol was heated at reflux for 24 hours resulting in precipitation of a solid. The solid was collected by filtration and washed with hot acetonitrile to give 3.0 g. of the desired product as a white solid, mp 276°–278° C.

EXAMPLE 53

N-[[[4-(Aminocarbonyl)phenyl]amino](benzoylimino)methyl]-N-methylbenzanide

A solution of 50.0 g of benzoylisothiocyanate in 400 ml. of diethyl ether was saturated with methylamine and the gaseous amine was bubbled through the solution for an additional hour. The pale yellow needles which formed were collected by filtration to give 16.0 g. of N-benzoyl-N'-methylthiourea, m.p. 143°–145° C. To 14.0 g. of this N-benzoyl-N'-methylthiourea, m.p. 143°–145° C. To 14.0 g. of this thiourea in acetone was added 11.0 g. of methyl iodide which, after 18 hours, provided 4.8 g. of 1-benzoyl-2,3-dimethylisothiourea hydroiodide, m.p. 126°–128° C. To 3.36 g. of this isothiourea hydroiodide, in 10 ml. of pyridine was added 1.2 ml. of benzoyl chloride. After three hours, this solution was poured into water and 1,3-bis-benzoyl-2,3-dimethylisothiourea was obtained as a yellow oil; $^1$H-NMR(tetramethylsilane standard in $CDCl_3$) showed phenyl protons at δ7.2–8.2 and methyl protons at δ2.35(S-methyl) and δ3.30(N-methyl). This yellow oil was refluxed in 35 ml. of iospropyl alcohol in the presence of 1.0 g. of p-aminobenzamide. A solid was obtained which was recrystallized from acetonitrile to give 0.65 g. of the title compound as colorless crystals, m.p. 132°–134° C.

EXAMPLE 54

N-[[[4-(Aminocarbonyl)phenyl]amino](benzoylimino)methyl]-N-butylbenzamide

To 17.9 g. of 1-butylthiourea in 100 ml. of acetone was added 11.4 ml of methyl iodide. After two hours at room temperature, this solution was diluted With 200 ml. of diethyl ether to give 34.2 g. of 1-butyl-2-methylisothiourea hydroiodide as colorless crystals, m.p. 90°–92° C. In 150 ml. of pyridine was dissolved 27.4 g. of this isothiourea, 30 ml. of benzoyl chloride was added, and the resultant reaction mixture was allowed to stand at room temperature for 18 hours and the poured into ice water. The aqueous layer was discarded while the 1,3-bis-benzoyl-2-butyl-3-methyl-isothiourea was recovered as a straw-colored water insoluble oil. This oil was reacted with 4-aminobenzamide as in Example 53 to provide the title compound.

EXAMPLE 55

N,N'-[[4-(Aminosulfonyl)phenyl]carbonimidoyl]bis(3-methylbenzamide)

A stirred mixture of 4.9 g. of 1,3-bis-(3-methylbenzoyl)-2-methylisothiourea and 2.8 g. of 4-aminobenzenesulfonamide in 300 ml. of isopropyl alcohol was refluxed for 6 hours. The mixture was filtered and the crystals that were collected were recrystallized from acetonitrile to give 2.0 g. of the title compound as colorless crystals, m.p. 224°≦225° C.

EXAMPLE 56

N,N'-[[4-(Aminosulfonyl)phenyl]carbonimidoyl]bisbenzamide

By the method of Example 55, 1,3-bisbenzoyl-2-methyl-isothiourea and 4-aminobenzenesulfonamide gave the title compound as colorless crystals, m.p. 250.5°–251.5° C.

EXAMPLE 57

N,N'-[[[4-(Aminosulfonyl)phenyl]methyl]carbonimidoyl]bisbenzamide

A stirred mixture of 4.4 g. of 4-aminomethylbenzenesulfonamide hydrochloride, 6.0 g. of 1,3-bisbenzoyl-2-methyl-isothiourea, and 3.0 g. of sodium acetate in 500 ml. of isopropyl alcohol was refluxed for 5 hours. The mixture was filtered and 10 g. of colorless crystals were collected. Recrystallization from acetonitrile gave 4.9 g. of title compound as colorless crystals, m.p. 165°–167° C.

EXAMPLE 58

N-[[[[4-(Aminosulfonyl)phenyl]methyl]amino][(4-methylbenzoyl)amino]methylene]-4-methoxybenzamide Using the method of Example 57, the interaction of 4-aminomethylbenzenesulfonamide hydrochloride with 1-(4-methoxybenzoyl)-3-(4-methylbenzoyl)-2-methylisothiourea provides the title compound as colorless crystals, m.p. 200°–203° C.

EXAMPLE 59

N-[[[[4-(Aminosulfonyl)phenyl]methyl]amino](benzoylimino)methyl]-N-ethylbenzamide To 36 g. of 1-ethylthiourea in 200 ml. of acetone was added 70 g. of methyliodide. Evaporation of the solvent gave 71 g. of 1-ethyl-2-methylisothiourea hydroiodide as colorless crystals, m.p. 84°–87° C. This isothiurea, 23.2 g., was reacted with a total of 30 ml. of benzoyl chloride and after 6 hours the solution was poured onto ice. The mixture was made basic with NaOH and the crystals which formed were collected by filtration to give 27.8 g. of 1,3-bisbenzoyl-1-ethyl-2-methylisothiourea, m.p. 84°–86° C. This bisbenzoylisothiourea, 3.1 g., was reacted with 2.4 g. of 4-aminomethylbenzenesulfonamide hydrochloride and 1.5 g. of sodium acetate in 250 ml. of isopropyl alcohol. Aqueous work-up followed by dichloromathane extraction and evaporation gave the title compound as a colorless glass, m.p. 70°–80° C.

We claim:

1. A compound of the formula:

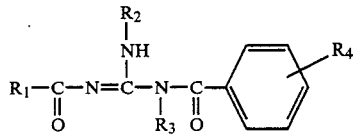

wherein $R_1$ is alkyl ($C_1$–$C_{10}$), biphenylyl, phenyl-alkyl($C_1$–$C_3$), phenoxyalkyl ($C_1$–$C_3$), naphthyl, cinnamenyl, adamantyl, cycloalkenyl ($C_5$–$C_7$) or a moiety of the formula:

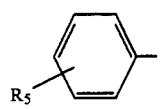

wherein $R_5$ is hydrogen, halogen trifluoromethyl, nitro, alkyl ($C_1$–$C_6$) or alkoxy ($C_1$–$C_3$); $R_2$ is dialkyl($C_1$–$C_3$)-aminoalkyl($C_1$–$C_3$) or a moiety of the formulae:

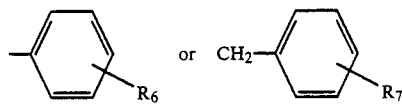

wherein $R_6$ is carbamoyl, sulfamoyl, alkyl($C_1$–$C_9$)aminocarbonyl or dialkyl($C_1$–$C_3$)aminocarbonyl and $R_7$ is carbamoyl or sulfamoyl; $R_3$ is hydrogen or alkyl($C_1$–$C_6$); and $R_4$ is hydrogen, halogen, trifluromethyl, nitro, alkyl($C_1$–$C_6$) or alkoxy($C_1$–$C_6$) or alkoxy($C_1$–$C_3$).

2. The compound in accordance with claim 1 wherein $R_1$ is phenyl, $R_2$ is 4-carbamoylphenyl, and $R_3$ and $R_4$ are both hydrogen.

3. The compound in accordance with claim 1 wherein $R_1$ is 4-trifluoromethylphenyl, $R_2$ is 2-(diethylamino)ethyl, $R_3$ is hydrogen, and $R_4$ is 4-trifluoromethyl.

4. The compound in accordance with claim 1 wherein $R_1$ is 3-tolyl, $R_2$ is 4-carbamoylphenyl, $R_3$ is hydrogen, and $R_4$ is 3-methyl.

5. The compound in accordance with claim 1 wherein $R_1$ is 3-tolyl, $R_2$ is 2-carbamoylphenyl, $R_3$ is hydrogen, and $R_4$ is 3-methyl.

6. The compound in accordance with claim 1 wherein $R_1$ is 4-bromophenyl, $R_2$ is 4-carbamoylphenyl, and $R_3$ and $R_4$ are both hydrogen.

7. The compound in accordance with claim 1 wherein $R_1$ is adamantyl, $R_2$ is 4-carbamoylphenyl, and $R_3$ and $R_4$ are both hydrogen.

8. The compound in accordance with claim 1 wherein $R_1$ is cinnamenyl, $R_2$ is 4-carbamoylphenyl, and $R_3$ and $R_4$ are both hydrogen.

9. The compound in accordance with claim 1 wherein $R_1$ is 4-methoxyphenyl, $R_2$ is 4-carbamoylphenyl, $R_3$ is hydrogen, and $R_4$ is 4-methyl.

10. The compound in accordance with claim 1 wherein $R_1$ is 4-trifluoromethylphenyl, $R_2$ is 4-carbamoylphenyl, $R_3$ is hydrogen, and $R_4$ is 4-methoxy.

11. The compound in accordance with claim 1 wherein $R_1$ is 4-fluorophenyl, $R_2$ is 4-carbamoylphenyl, $R_3$ is hydrogen, and $R_4$ is 4-bromo.

12. The compound in accordance with claim 1 wherein $R_1$ is 3-bromophenyl, $R_2$ is 4-carbamoylphenyl, and $R_3$ and $R_4$ are both hydrogen.

13. The compound in accordance with claim 1 wherein $R_1$ is 3-tolyl, $R_2$ is 4-carbamoylphenyl, $R_3$ is hydrogen, and $R_4$ is 4-methoxy.

14. A method of meliorating anxiety in a warm-blooded animal which comprises administering internally to said warm-blooded animal an effective antianxiety amount of a compound of claim 1.

15. A method of treating cognitive and related neural behavioral problems in warm-blooded animals which comprises administering internally to said warm-blooded animal an effective amount of a compound of claim 1.

16. An antianxiety composition of matter in dosage unit form comprising from about 35 mg to about 250 mg per dosage unit of a compound of claim 1 in association with a pharmaceutically acceptable carrier.

17. A neurotropic composition of matter in dosage unit form comprising from about 50 mg to about 250 mg per dosage unit of a compound of claim 1 in association with a pharmacutically acceptable carrier.

* * * * *